US007112562B2

(12) United States Patent
Tchelingerian

(10) Patent No.: US 7,112,562 B2
(45) Date of Patent: Sep. 26, 2006

(54) INSULIN CONJUGATES AND METHODS OF USE THEREOF

(75) Inventor: Jean-Leon Tchelingerian, Paris (FR)

(73) Assignee: Diatos, S.A., Paris (FR)

( * ) Notice: Subject to any disclaimer, the term of this patent is extended or adjusted under 35 U.S.C. 154(b) by 0 days.

(21) Appl. No.: 11/327,647

(22) Filed: Jan. 9, 2006

(65) Prior Publication Data

US 2006/0166889 A1    Jul. 27, 2006

Related U.S. Application Data

(62) Division of application No. 10/231,894, filed on Aug. 29, 2002, now Pat. No. 7,049,286.

(60) Provisional application No. 60/316,063, filed on Aug. 30, 2001.

(51) Int. Cl.
    A61K 38/00    (2006.01)
(52) U.S. Cl. ......................................................... 514/3
(58) Field of Classification Search ..................... 514/3
    See application file for complete search history.

(56) References Cited

U.S. PATENT DOCUMENTS

| 5,547,929 | A | 8/1996 | Anderson et al. |
| 5,624,894 | A | 4/1997 | Bodor |
| 6,066,485 | A | 5/2000 | Guthridge et al. |
| 6,855,801 | B1 | 2/2005 | San Antonio |

FOREIGN PATENT DOCUMENTS

| FR | 2766826 | 2/1999 |
| WO | WO 96/06632 | 3/1996 |
| WO | WO 97/02840 | 1/1997 |
| WO | WO 99/07414 | 2/1999 |
| WO | WO 99/32136 | 7/1999 |
| WO | WO 00/45831 | 8/2000 |
| WO | WO 01/64738 | 9/2001 |

OTHER PUBLICATIONS

Amara, et al., J. Biol. Chem., vol. 274, pp. 200-204, 1999.
Arkonac, et al., J. Biol. Chem., vol. 273, pp. 4400-4405, 1998.
Avrameas, et al., Proc. Natl. Acad. Sci., vol. 95, p. 5601, 1998.
Campanelli, et al., Development, vol. 122, p. 1663-1672, 1996.
Cardin, et al., Biochem. Biophys. Res. Com., vol. 154, p. 741, 1988.
Cardin & Weintraub, Arteriosclerosis, vol. 9, p. 21, 1989.
David, FASEB J., vol. 7, p. 1023, 1993.
Fowlkes, et al., Endocrinol., vol. 138, p. 2280-2285, 1997.
Fromm, et al., Arch. Biochem. Bioph., vol. 343, p. 92, 1997.
GenBank Accession No. 600165A.
GenBank Accession No. 550085A.
GenBank Accession No. AAH05255.
GenBank Accession No. AAA59179.
Xu, et al., Glyconjug J., vol. 13, p. 81-90, 1996.
Hasan, et al., J. Immunol., vol. 162, p. 1064-1070, 1999.
Hirabayashi, et al., Scand. J. Immunol., vol. 37, p. 533, 1993.
Inoue, et al., FEBS, vol. 269, p. 89-92, 1990.
Javadpour, et al., J. Med. Chem., vol. 39, pp. 3107-3113, 1996.
Kalsi, et al., Lupus, vol. 4, p. 375, 1995.
Lortat-Jacob & Grimaud, FEBS, vol. 280, pp. 152-154, 1991.
Maher, et al., Mol. Cell. Biol., vol. 9, p. 2251-2253, 1989.
Merton, et al., Annu. Rev. Cell. Biol., vol. 8, p. 365, 1992.
Pohl, et al., FEBS, vol. 272, p. 200-204, 1990.
Stevenson, et al., J. Autoimmunity, vol. 6, p. 809, 1993.
Yayon, et al., Cell, vol. 64, p. 841-848, 1991.
Stoll, et al., J. Controlled Release, vol. 64, p. 217-228, 2000.
Partial International Search Report for PCT/IB02/03916, mailed Jun. 23, 2003.
PCT International Search Report dated Sep. 17, 2003.
PCT Written Opinion for PCT/IB02/03916.

*Primary Examiner*—Cecilia J. Tsang
*Assistant Examiner*—Maury Audet
(74) *Attorney, Agent, or Firm*—Hunton & Williams LLP

(57) ABSTRACT

The invention relates generally to chimeric peptides and compositions that facilitate the transport of insulin across biological membranes, methods for preparing the chimeric peptides, and a method for treating a subject suffering from diabetes.

16 Claims, 5 Drawing Sheets

INSULIN CONJUGATES AND METHODS OF USE THEREOF

CROSS-REFERENCE TO RELATED APPLICATIONS

This application is a divisional of U.S. patent application Ser. No. 10/231,894, filed Aug. 29, 2002, which claims the benefit of priority from U.S. Provisional Application No. 60/316,063, filed Aug. 30, 2001, the disclosures of each of which are incorporated herein by reference in their entireties.

FIELD OF THE INVENTION

The invention relates generally to composition and methods of treating diabetes and more particularly to compositions that increase blood insulin levels.

BACKGROUND OF THE INVENTION

Diabetes is a disease that afflicts close to 16 million Americans. Type I diabetes, or juvenile diabetes, is characterized by absolute insulin deficiency and dependence on exogenous insulin to sustain life. Approximately 800,000–1.6 million people have been diagnosed with type I diabetes. Type II diabetes results from a metabolic disorder in which the body does not properly use the insulin it produces. Approximately 15 million people have type II diabetes. Total cost (indirect and direct) exceeds 98 billion dollars.

Current long-term treatment of type I diabetes relies predominantly on subcutaneous injection of exogenous insulin. This treatment however does not provide optimal metabolic control, as this therapy is not able to mimic the delicate minute-by-minute modulation of insulin secretion, which normally occurs in relation to meals, exercise, etc. Even with the advent of biotechnology to produce many different types of insulin, which vary in their onset, peak, and duration of action, it is still difficult to properly control glucose levels throughout the day. When diabetics inject insulin, peripheral tissues are exposed to higher levels of insulin so that it is more difficult to properly regulate liver metabolism in these patients. Although good metabolic control with near normal glycemia has been demonstrated by using multiple (2–4) daily injections, the inconvenience of such a large number of injections precludes a widespread use of this regiment.

The most convenient, comfortable, acceptable, and easiest delivery route would be oral. The gastrointestinal (GI) mucosa offers several advantages as an administration site over other mucus membranes. These advantages include the following: (1) the oral administration route is familiar, convenient, and an accepted means of dosing for most people; (2) the GI epithelium offers a large surface area for absorption; and (3) the GI epithelium provides a close connection with a vast blood supply. Hormones, such as insulin, are administered via the subcutaneous route, because they are unable to get past the harsh environment of the upper gastrointestinal tract. Unlike subcutaneous injections, oral delivery of insulin would be able to mimic the transport of physiologic insulin from the pancreas to the hepatic portal circulation, as seen in healthy non-diabetic individuals. However, oral delivery of insulin intact is believed to be virtually impossible. No more than 0.5% of orally administered insulin is absorbed under the best experimental conditions. Even if a little of the insulin is able to miraculously pass through the upper gastrointestinal tract, the hormone is fairly large and hydrophillic, rendering it incapable of crossing through the intestinal barrier.

SUMMARY OF THE INVENTION

The invention relates to chimeric insulin peptides that chimeric insulin peptides that are useful for increasing serum insulin concentration and decreasing serum glucose concentration. Also provide by the invention are method of treating a subject suffering from diabetes, i.e., Type I or Type II.

The compositions of the invention are based in part on the discovery that Diatos peptide vectors (DPVs) allow for transport of molecules that would normally be unable to be transported across a physiological barrier, and more specifically, the intestinal epithelial barrier. For example, macromolecules such as insulin can be transported across the intestinal epithelial barrier using the DPVs described herein.

In various aspects the invention provides a chimeric peptide. The chimeric peptide can translocate a biological membrane such as a plasma membrane, mitochondrial membrane or nuclear membrane. Alternatively the chimeric peptide translocates a physiological barrier such as the gastrointestinal barrier, the blood-brain barrier, the skin barrier, the airway epithelium barrier, the trans-mucosal barrier, the intra-nasal barrier and the ocular barrier.

In one aspect, the invention provides a chimeric peptide having a first domain and a second domain. The first domain is a translocation sequence which facilitates active transport across a biological membrane, The second domain is at least a portion of an insulin polypeptide.

The translocation sequence is a portion of a lipoprotein. Additionally, the translocation sequence is at least 4 basic amino acids, e.g. lysine, or arginine. Preferably, the translocation sequence that binds to an aminoglycan such as heparin or chondroitin sulfate.

The first domain is an amino acid sequence selected from the group consisting of a) $(XBBBXXBX)_n$; b) $(XBBXBX)_n$; c) $(BBX_mBBX_o)_n$; d) $(XBBXXBX)_n$; and e) $(BXBB)_n$, wherein B is a basic amino acid; X is a non-basic amino acid; each m is independently an integer from zero to five; each n is independently an integer between one and ten; and each o is independently an integer between zero to five. In certain embodiments n may be 2 or 3 and X may be a hydrophobic amino acid.

The amino acid sequence of the first domain is less than 100 amino acids long; less than 50 amino acids long; less than 25 amino acids long. Preferably, first domain amino acid sequences are GKRKKKGKLGKKRDP (SEQ ID NO:30, DPV7) or SSRRARRSPRHLGSG (SEQ ID NO:35, DPV10).

The chimeric peptide may further comprise an amino acid sequence of a antibody fragment such as a) a CDR3 region of a human anti-DNA antibody; b) a CDR2 region of a human anti-DNA antibody; c) a CDR3 region of a murine anti-DNA antibody; and d) a CDR2 region of a murine anti-DNA antibody.

In other aspects, the invention provides a chimeric peptide having a first domain, a second domain, and a third domain. The first domain and second domain comprises an amino acid sequence of a) $(XBBBXXBX)_n$; b) $(XBBXBX)_n$; c) $(BBX_mBBX_o)_n$; d) $(XBBXXBX)_n$; e) $(BXBB)_n$ or f) (an antibody fragment)$_n$, wherein B is a basic amino acid; X is a non-basic amino acid; each m is independently an integer from zero to five; each n is independently an integer between one and ten; each o is independently an integer between zero to five. The first domain is different from the second domain. The third domain is at least a portion of an insulin polypeptide. The chimeric peptide translocates across a biological membrane or a physiological barrier.

In yet another aspect, the invention provides a chimeric peptide comprising a) at least a portion of a CDR3 region of an anti-DNA antibody; and b) at least a portion of a CDR2 region of an anti-DNA antibody and c) at least a portion of an insulin polypeptide, wherein the peptide translocates a biological membrane.

The invention also provides compositions of the chimeric peptide and a carrier. The composition suitable for oral administration.

In another aspect, the invention provides a kit comprising the composition of the invention.

The invention also provides methods for decreasing glucose levels or increasing insulin levels in a cell by contacting the cell with the compositions of the invention. Alternatively, glucose levels are decreased insulin levels increased in the serum of a subject by administering to the subject in need thereof the compositions of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

DETAILED DESCRIPTION OF THE INVENTION

Figure 1:
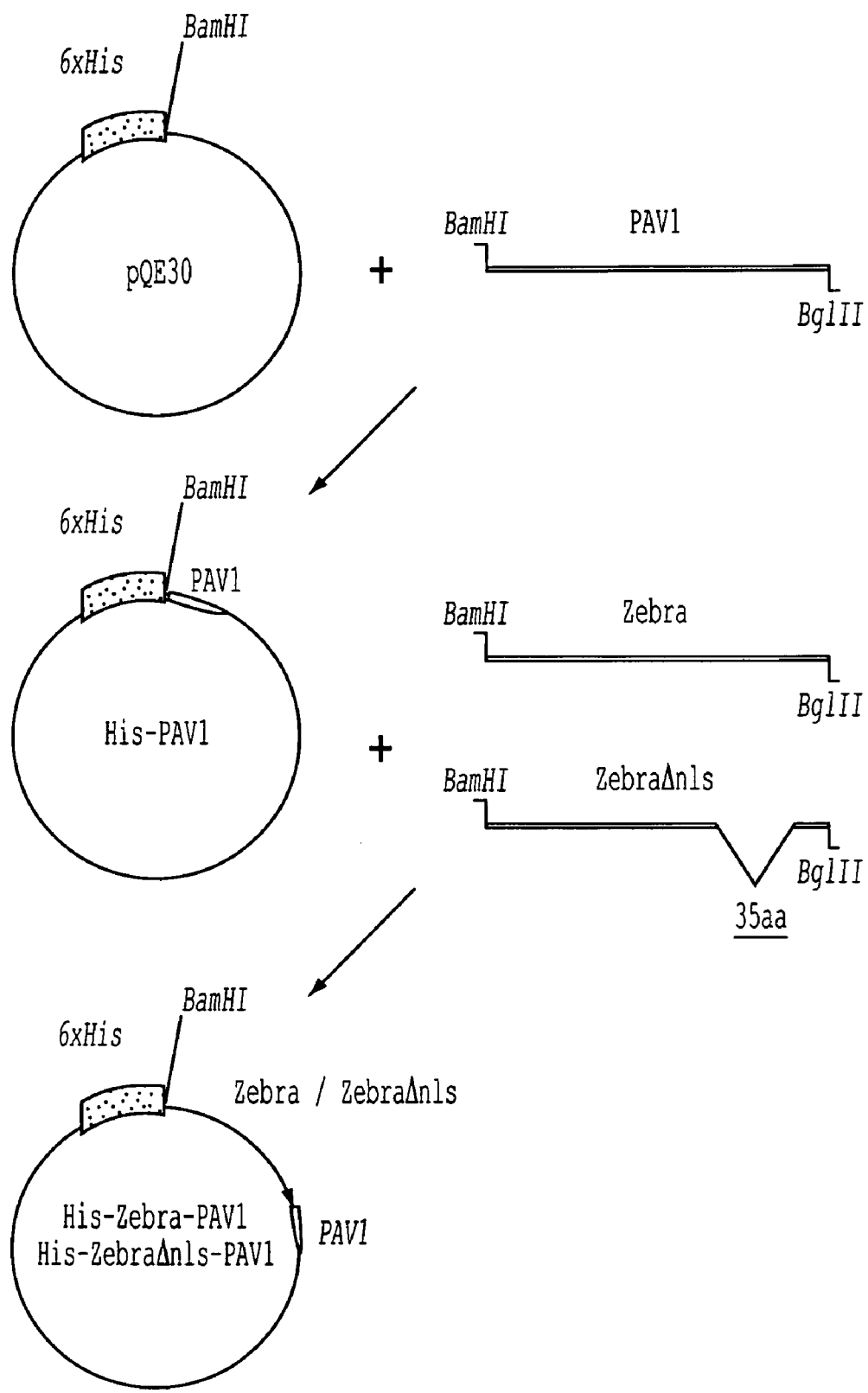
FIG. 1 shows a schematic description of the preparation of vectors for the expression of recombinant proteins containing the peptides of the invention.

The invention provides compositions containing chimeric insulin peptides that are useful for increasing serum insulin concentration and decreasing serum glucose concentration. The chimeric peptides can be used to modulate the bioavailability of insulin in a subject. The chimeric peptides of the invention, or nucleic acids encoding these chimeric peptides, can be incorporated into pharmaceutical compositions and administered to a subject to treat diabetes i.e., Type I or Type II.

In various aspects the invention provides a chimeric peptide that include a first domain containing a translocation sequence operably linked to a second domain containing at least a portion of an insulin polypeptide. The first and second domains can occur in any order in the peptide, and the peptide can include one or more of each domain.

As used herein, "chimeric protein" or "chimeric peptide" includes at least a portion of an insulin polypeptide operatively linked to a non-insulin polypeptide. An "insulin polypeptide" refers to a polypeptide having an amino acid sequence or corresponding to at least a portion of a insulin polypeptide or a nucleic acid encoding for a polypeptide having an amino acid sequence or corresponding to at least a portion of a insulin polypeptide, whereas a "non-insulin polypeptide" refers to a polypeptide having an amino acid sequence corresponding to a protein that is not substantially homologous to the insulin, e.g., a protein that is different from the insulin polypeptide or fragment and that is derived from the same or a different organism. Within a insulin chimeric peptide the insulin polypeptide can correspond to all or a portion of an insulin polypeptide.

The term "operatively linked" is intended to indicate that the first and second domains are chemically linked (most typically via a covalent bond such as a peptide bond) in a manner that allows for at least one function associated with a insulin polypeptide. When used to refer to nucleic acids encoding a chimeric peptide, the term operatively linked means that a nucleic acid encoding the first domain and the insulin polypeptide are fused in-frame to each other. The first domain can be fused to the N-terminus or C-terminus of the insulin polypeptide.

A "translocation sequence" refers to any sequence of amino acids that directs a peptide in which it is present to a desired cellular destination. Thus, the translocation sequence can direct or facilitate penetration of the peptide across a biological membrane, e.g., a phospholipid membrane, mitochondrial membrane, or nuclear membrane. For example the translocation sequence directs the peptide from outside the cell, through the plasma membrane, and into the cytoplasm or to a desired location within the cell, e.g., the nucleus, the ribosome, the mitochondria, the ER, a lysosome, or peroxisome. Alternatively, or in addition, the translocation sequence can direct the peptide across a physiological barrier such as the blood-brain barrier, the transmucosal barrier, or the hematoencephalic, hematoretinal, gastrointestinal and pulmonary barriers.

Translocation, i.e., penetration across a biological membrane or physiological barrier can be determined by various processes, for example by a cell penetration test having a first incubation step for the chimeric peptide in the presence of culture cells, followed by a fixing step and permeabilization of those cells, and then revelation of the presence of the chimeric peptide inside the cell. The revelation step can be done with another incubation in the presence of antibodies marked and directed against the chimeric peptide, followed by detection in the cytoplasm or in immediate proximity of the cell nucleus, or even within it, of the immunologic reaction between the sequence and the marked antibodies. Revelation can also be done by marking an amino acid sequence in the invention and detecting the presence of the marking in the cell compartments. A cell penetration test was described in the above-mentioned patent application No. WO 97/02840.

Translocation can require energy, i.e., active transport. Alternatively, translocation does not require energy, i.e., passive transport.

A translocation sequence can be of any length. For example translocation sequence is less than 600 amino acids in length, e.g., less than or equal to 500, 250, 150, 100, 50, 25, or 10 amino acids in length. The translocation sequence is composed of at least four basic amino acids.

The translocation sequence is derived from a known sequence. For example, the translocation sequence may include sequences from a lipoprotein, such human lipoprotein B, human lipoprotein E; an immunoglobulin molecule, such as the CDR2 or CDR3 region; agrine; FGF; or PGF.

Preferably, the translocation is further characterized by its ability to react with heparin, chondroitin sulfate and their derivatives. The peptides binding to glycosaminoglycans (GAG) or, more generally, to the aminoglycans, and in particular to heparin, heparin sulfate and the chondroitin sulfates can be natural in origin, like the peptides described above, or artificial. They can be used in their natural or polymer (dimer, trimer, etc.) form. "Heparin or chondroitin sulfate derivatives" or "aminoglycans like heparin or chondroitin sulfate" are understood to mean any product or sub-product as defined in the publications cited in references (Cardin & Weintraub, Arteriosclerosis 9:21 (1989); Merton et al., Annu. Rev. Cell Biol. 8:365 (1992); David, FASEB J. 7:1023 (1993)).

Examples of the translocation sequence include a peptide which includes the amino acid sequence having with one of the following formulae a) $(XBBBXXBX)_n$; b) $(XBBXBX)_n$; c) $(BBX_mBBX_o)_n$; d) $(XBBXXBX)_n$; e) $(BXBB)_n$, or f) (an antibody fragment)$_n$, wherein B is a basic amino acid; X is a non-basic, preferably hydrophobic amino acid, such as alanine, isoleucine, leucine, methionine, phenylalanine, tryptophan, valine or tyrosine; m is a whole number between 0 and 5; n is a whole number between 1 and 10, preferably between 1 and 3; and o is a whole number between 0 and 5.

An antibody fragment is meant to include less than full-length immunoglobulin polypeptide, e.g., a heavy chain, light chain, Fab, $Fab_2$, Fv, or Fc. The antibody can be for example human or murine. Preferably the antibody is an anti-DNA antibody. Preferably, the antibody fragment contains all or part of the CDR2 region of an antibody. Alternatively, the antibody contains all or part of the CDR3 region of an antibody. More specifically, the antibody fragment contains at least one CDR3 region of an anti-DNA human antibody, such as RTT79, NE-1 and RT72.

By "all or part" it is understood that the antibody fragment can contain either the whole CDR region concerned, or only part of it, provided that the vector retains the capacity to penetrate into the cells (functional homologue). By "part of CDR region" is understood a CDR region deprived of one or more terminal amino acids. It can also be a CDR region in which one or more internal residues have been deleted or substituted for other amino acids, preferably amino acids of the same nature (basic amino acids, for example).

Exemplary translocatable sequences include SEQ ID NOs:1–48. Preferred translocatable amino acid sequences are GKRKKKGKLGKKRDP (SEQ ID NO:30) and SSRRARRSPRHLGSG (SEQ ID NO:35). Generally, the amino acid sequence of the first domain is less than 100 amino acids long; less than 50 amino acids long; or less than 25 amino acids long. Preferably, the first domain is between 6 and 25 amino acids.

As used herein the term "insulin" shall be interpreted to encompass insulin analogs, natural extracted insulin, or recombinantly produced insulin that is biologically active. By biologically active is meant the molecule has the ability to suppress or prevent disease symptoms of diabetes, e.g. decrease serum glucose. Biologically active insulin includes preproinsulin, proinsulin, insulin alpha chain, insulin beta chain and mature insulin, e.g., alpha and beta chain. The insulin can be derived from any species such as human, bovine, porcine, equine, canine or murine.

The term is intended to encompass the polypeptide normally used in the treatment of diabetes in a substantially purified form but encompasses the use of the term in its commercially available pharmaceutical form, which includes additional excipients. Insulin for use in the present invention can be obtained from numerous commercial sources such as Novo Laboratories (Danbury, Conn.), Nordisk-USA (Rockville, Md.) and Eli Lilly and Co. (Indianapolis, Id.).

Porcine-derived insulin, human semi-synthetic insulin (Nordisk-USA) and cloned recombinant insulin (Eli Lilly) can be used when practicing the method of the present invention. The insulin is preferably recombinantly produced and may be dehydrated or in solution.

The term "insulin analog" and the like are used interchangeably herein and are intended to encompass any form of "insulin" as defined above, wherein one or more of the amino acids within the polypeptide chain has been replaced with an alternative amino acid and/or wherein one or more of the amino acids has been deleted or wherein one or more additional amino acids has been added to the polypeptide chain or amino acid sequences, which still has at least one function of native insulin such as for example, decreasing blood glucose levels. In general, the term "insulin analogs" of the present invention include "insulin lispro analogs", as disclosed in U.S. Pat. No. 5,547,929, incorporated hereinto by reference in its entirety; insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin, such as insulin lispro, i.e., compounds which are administered to reduce blood glucose levels.

Novel insulin A-chain mutants are also useful in this invention. The human insulin A-chain analogue preserves the native intra-molecular disulfide bond between the residues $Cys^{A6}$ and $Cys^{A11}$ and two serines in positions 7 and 30 replace the cysteines implied in the two interchain disulfide bridge formed with the B-chain in the native insulin.

The insulin polypeptide, and/or nucleic acid encoding an insulin polypeptide can be constructed using insulin encoding sequences are known in the art. Sources for insulin polypeptides and nucleic acids encoding insulin polypeptides include GenBank Accession Nos. 600165A; 550085A; AAH05255; AAA59179 and are incorporated herein by reference in their entirety.

Exemplary insulin molecules include, but are not limited to,

GIVEQCCTSICSLYQLENYCNFVNQHLCGSHLVEAL-YLVCGERGFFYTPKT (SEQ ID NO: 52, human insulin);

GIVEQCCTSICSLYQLENYCNFVNQHLCGSHLVEAL-YLVCGERGFFYTKPT (SEQ ID NO: 53, human lyspro insulin);

GIVEQCSTSICSLYQLENYSNFVNQHLCGSHLVEAL-YLVCGERGFFYTPKT (SEQ ID NO: 54, human "mini-insulin");

GIVEQCCASVCSLYQLENYCNFVNQHLCGSHLVEAL-YLVCGERGFFYTPKA (SEQ ID NO: 55, bovine insulin); and GIVEQCCTSICSLYQLENYCNFVNQHLCGSHLVEAL-YLVCGERGFFYTPKA (SEQ ID NO: 56, porcine insulin).

If desired, one or more amino acids can additionally be inserted between the first peptide moiety comprising the translocation sequence and the second polypeptide moiety comprising insulin. In some embodiments, the first or second domain includes a sequence that facilitates association of the translocation sequence with insulin.

In one embodiment, a chimeric peptide comprises at least one biologically active portion of a insulin polypeptide. In another embodiment, a chimeric peptide comprises at least two biologically active portions of an insulin polypeptide. In yet another embodiment, a chimeric peptide comprises at least three biologically active portions of a insulin polypeptide.

The translocation sequence and insulin sequence can be linked by chemical coupling in any suitable manner known in the art. Many known chemical cross-linking methods are non-specific, i.e.; they do not direct the point of coupling to any particular site on translocation sequence or the insulin. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, CHEMICAL MODIFICATION OF PROTEINS, Holden-Day, 1974, pp. 39–43. Among these reagents are, for example, J-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonyl-chloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-liking reagent is bismaleimidohexane ("BMH"). BMH contains two maleimide functional groups, which react specifically with sulfhydryl-containing compounds under mild conditions (pH 6.5–7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl) cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidyl-propionate) ("DSP"), and N-succinimidyl 3-(2-pyridyldithio) propionate ("SPDP") are well-known cleavable cross-linkers. The use of a cleavable cross-linking reagent permits insulin to separate from the translocation sequence after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, Chemistry Of Protein Conjugation And Cross-Linking, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651 H).

The chimeric peptide protein may be linked to one or more additional moieties. For example, the chimeric peptide may additionally be linked to a GST protein in which the chimeric peptide is fused to the C-terminus of the GST (i.e., glutathione S-transferase) sequences. Such fusion proteins can facilitate the purification of chimeric peptide.

Alternatively, the chimeric peptide can be produced as a fusion peptide that includes the translocation sequence and the insulin sequence which can conveniently be expressed in known suitable host cells. Fusion peptides, as described herein, can be formed and used in ways analogous to or readily adaptable from standard recombinant DNA techniques.

Generally, the amino acid sequences of the invention (SEQ ID NOs: 1–48) include a high number of basic amino acids, as is the case in lysine, arginine or histidine, for example. "High number" should be understood as at least equal to 3.

One particularly interesting amino acid sequence is the sequence SEQ ID NO: 1, to the extent that (1) in the state at least of dimer, it has the desired properties and (2) in the state of monomer or polymer, it gives another amino acid sequence to which it is coupled the properties or substantially potentiates those properties when the sequence already has them. Similarly, the peptides designated DPV3, (DPV3)$_2$, DPV6, DPV7, DPV10 and DPV13 have this potentiation capacity.

The invention also provide methods of increasing serum insulin level or decreasing serum or intracellualar glucose levels. Serum glusose levels are decreased or insulin level are increases in a subject in need thereof. Increasing serum or intracellular insulin level or decreasing serum or intracellualar glucose levels by administering a composition containing a chimeric peptide of the invention. A subject is identified by measuring either serum glucose or insulin levels by methods know in the art. A subject is in need of increased serum insulin or decreased glucose levels if the subjects insulin or glucose levels are not in normal ranges. Normal glusose levels are 60–120 mg/dl. Normal insulin levels are 7 mU/mL±3 mU. For example if the subjects serum glucose levels are greater than 120 mg/dl, the subject requires a decrease in serum glucose level. In contrast in the subjects glucose levels are between 60–120 mg/dl, serum glucose level need not be decreased. Preferably, after administration the subjects serum glucose is between at least 60–120 mg/dl. A subject is in need of increased insulin levels, if for example, serum insulin levels are less than 4 mU/mL. Preferably, after administration serum insulin levels are the serum insulin levels are 7 mU/mL±3 mU.

Additionally, the invention provides a method of treating or preventing diabetes by administering to a subject in which such treatment or prevention is desired composition containing a chimeric peptide of the invention in an amount sufficient to treat or prevent the disease in the subject. Efficaciousness of treatment is determined in association with any known method for diagnosing or treating diabetes Diabetes is diagnosed for example, by excessive urination intense thirst and hunger severe fatigue dry skin or unexplained weight loss The subject can be e.g., any mammal, e.g., a human, a primate, mouse, rat, dog, cat, cow, horse, pig.

The chimeric peptides, or nucleic acid molecules encoding these chimeric peptides (also referred to herein as "Therapeutics" or "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents disclosed herein can also be formulated as liposomes. Liposomes are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a glycoprotein Ibα fusion protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Sustained-release preparations can be prepared, if desired. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

As examples, the oral dosages of the chimeric peptides of the invention, when they are used for the effects indicated, will be between around 0.05 and 1,000 mg/day by the oral route and, preferably come in the form of tablets containing 0.5, 1.0, 2.5, 5.0, 10.0, 15.0, 25.0, 50.0, 100.0, 250.0, 500.0 and 1,000.0 mg of active ingredient. The effective plasma levels of the vectors or transporters loaded with at least one substance of interest will range from 0.002 mg to 50 mg per kilogram of body weight and per day.

The chimeric peptides or nucleic acid encoding the chimeric peptides of the invention, 1 may be administered in the form of single daily doses, or the total daily dose may be administered in two, three or four doses per day.

The pharmaceutical compositions can be included in a container, kit, pack, or dispenser together with instructions for administration.

In one particular application, this invention relates to a diagnostic agent for in vitro use, composed of or containing at least one chimeric peptide and/or one cell according to the invention. Such a diagnostic agent can also be used in vivo.

The subject of this invention is therefore also a diagnostic kit that includes the diagnostic agent. More specifically, the diagnostic kit includes a predetermined quantity of a composition in the invention, in one or more containers.

In another embodiment, the invention provides a method of translocating a substance of interest across a biological membrane of a eukaryotic cell, the method comprising providing a chimeric peptide of the invention and contacting a cell culture in the presence of the chimeric peptide. In one embodiment the cell culture is contacted with the chimeric peptide under conditions that promote active metabolism of the eukaryotic cell.

The invention also provides a method of increasing the intracellular concentration or decreasing intracellular glucose concentration of insulin within a eukaryotic cell, by contacting the cell with a chimeric peptide of the invention under conditions promoting active metabolism of the eukaryotic cell.

In another aspect, the invention provides for a method for producing a peptide of the invention comprising transfecting a production cell with a vector comprising a nucleic acid molecule encoding the peptide operably linked to an expression control sequence, culturing the production cell under conditions that permit production of the peptide, and isolating the peptide.

The invention includes the use of the chimeric peptides as defined above as peptide vectors. As used herein the term "chimeric peptide", "vector" and "peptide vector" can be used interchangeably. These vectors are capable of transporting inside cells insulin that is combined with them covalently or non-covalently, and are thus effective vectors for intracellular transfer of insulin.

To achieve this goal, it is necessary for a vector to be capable of transporting relatively large quantities of molecules inside cells and for it not to be recognized as a foreign antigen by the human immune system.

It has been found that these chimeric peptides can be used both in vivo and in vitro as agents for internalizing insulin inside cells.

As a variation, the vector is based on coupling, on one hand, of amino acid sequences reacting with aminoglycans and, on the other hand, of new peptides derived from the variable part of human anti-DNA antibodies. "Coupling" is understood to mean any type of interaction allowing a physical association between an insulin polypeptide and the diatos peptide vector. It can be cleavable or non-cleavable according to the biological medium and/or the substance of interest transported by the peptides of the invention or it can be cleavable by physical means applied to the organism to which the vector coupled to the active substance has been administered. Thus, the expression of the biological effect of the substance can require that it be released from the vector.

The coupling of amino acid sequences reacting with aminoglycans and peptides derived from variable parts of human anti-DNA antibodies inside one and the same molecule results in the preparation of a peptide vector that is particularly effective in translocation and intracellular transfer of insulin, above all when the amino acid sequences reacting with the aminoglycans are human in origin.

This combination also gives rise to a translocation and transfer vector specially adapted for use in humans. Indeed, as indicated above, although the peptide vectors of murine origin known from WO 97/02840 are coded by the germinal line and carry no mutations, and consequently should be close to those encountered in humans in terms of antigens, it is possible that their injection into humans would induce an immune reaction. The peptide vector formed from DPV according to the invention and from peptides derived from anti-DNA antibodies, both of human origin, coded by the germinal line and carrying no mutations, prevents this problem.

The general characteristics of these peptides derived from human anti-DNA antibodies are close to those of the peptides of murine origin described in publication WO 99/07414, while they have additional properties that distinguish them from the latter, namely:

1) The ability to penetrate inside cells, they have to have an active cell metabolism (culture temperature between 25° C. and 39° C., preferably and 37° C.), while the murine peptides are clearly less dependent;

2) They react much less strongly with DNA than the murine vectors;

3) Their penetration capacity is not significantly influenced by the molecule they are going to transport inside the cell;

4) They penetrate better inside cells of human origin than inside cells of other origins.

The invention provides a diatos peptide vector composed of a heparin-binding peptide and one or more antibody fragments, preferably polyreactive, and more specifically one or more fragments that come from hypervariable regions of the antibody. Preferably, the vector that is the subject of the invention is characterized by the fact that it contains a fragment of the heavy chain of an antibody.

In the above-mentioned patent application WO 99/07414, only fragments of a monoclonal IgG were used, which is a monomer immunoglobulin that is small in size and has a low molecular weight. The invention shows that it is also possible to use a fragment that comes from an IgM, which is a pentamer immunoglobulin, with a very high molecular weight.

As indicated above, the vector of the invention is particularly well suited for intracellular and intranuclear transport and transfer of insulin.

Unlike other techniques of internalization of a substance of interest into a cell, the techniques of the present invention rely on energy. Penetration of the peptides is completely inhibited by incubating the cells at 4° C. It is also partly inhibited by inhibitors of cell metabolism, like sodium azide (inhibitor of ATPase) and genistein (inhibitor of tyrosine kinase and the bond to ATP). Therefore the mechanism for internalization of the peptides of the invention, and hence of the substances of interest coupled to the peptides, is dependent on energy. The vectorization using the peptides of the invention is therefore done via a binding site at the surface of cells. The amino acid sequences of the invention are therefore characterized by their capacity to be fixed to a binding site located on the cell membrane and to cross the cell membrane. Thus, the amino acid sequences of the invention are characterized by their capacity to be able to cross the cell membranes by an active mechanism, then to lodge in the cytoplasm and/or cell nucleus. They are therefore distinguished from the peptide transporters in the prior art that were capable of crossing the cell membrane in a passive way.

It is thus possible to have a vector whose use is not limited, when it passes into the cell, by the size of the substances being transported. Indeed, the vectors of the invention are capable of transporting drugs, ranging from small chemical molecules (low molecular weight) to proteins or plasmid-type nucleic acids (high molecular weight). This special capacity of the vectors of the invention for penetration makes it possible to target "drugs" in the cells in a preferential way, thus contributing to a potential reduction in the toxicity of the drugs and a potential increase in the efficacy index.

The invention is therefore aimed at supplying a vector such as the one described above, characterized by the fact that it contains a substance of interest naturally, or not naturally, that can be incorporated into the cells and/or the nuclei of the cells.

More specifically, the subject of the invention is a vector whose penetration capacity is quite independent from the nature of the substance of interest that is coupled to it. This characteristic, proper to these human vectors compared to the murine vectors, is of primary interest in the planned use of these vectors. But the invention is also interested in vectors that are adapted to the substance of interest which is coupled to it.

However, the interaction must be solid enough that the vector does not dissociate before or during cell penetration. For this reason, the coupling preferred in the invention is covalent coupling, although it can be non-covalent coupling. The insulin polypeptide can be coupled directly to the peptide either on one of those terminal ends or on a side chain or one of the amino acids. The insulin polypeptide can also be coupled indirectly by a connecting arm either to one of the terminal ends of the peptides or to a side chain of one of the amino acids.

It has also been shown that the vector of the invention permits transfection of cells in vitro.

In one embodiment of the invention, the vector is coupled to the insulin polypeptide by at least one molecule (called an "anchoring molecule") that has a strong natural affinity for the insulin polypeptide. The natural affinity of the anchoring molecule for the insulin polypeptide allows the transporter to interact non-covalently with the insulin polypeptide, and hence to carry it along in intracellular travel.

Another especially interesting advantage of this type of transporter consists of the fact that, due to the natural affinity of the anchoring molecule for the insulin polypeptide, these two elements are coupled in a totally natural way, with no chemical or biochemical interaction.

This type of transporter is particularly interesting in a case where the substance of interest, due to its size and/or its structure, proves difficult to couple directly to the amino acid sequence. This type of transporter can also prove particularly useful when the substance of interest is not very stable, and when any kind of chemical interaction for coupling it could degrade it or alter its activity.

Another aspect of the invention pertains to vectors, preferably expression vectors, containing a nucleic acid encoding a chimeric peptide, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionaly, some viral vectors are capable of targeting a particular cells type either specifically or non-specifically.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., chimeric peptides, mutant forms of the chimeric peptide, fusion proteins, etc.).

The recombinant expression vectors of the invention can be designed for expression of the chimeric peptide in prokaryotic or eukaryotic cells. For example, the chimeric peptide can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the chimeric peptide expression vector is a yeast expression vector. Examples of vectors for expression in yeast *S. cerevisiae* include pYepSec1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, the chimeric peptide can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Additionally, host cells could be modulated once expressing the chimeric peptide, and may either maintain or loose original characteristics.

A host cell can be any prokaryotic or eukaryotic cell. For example, chimeric peptide can be expressed in bacterial cells such as *E. coli*, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA can be introduced into prokaryotic or eukaryotic cells via conventional transformation, transduction, infection or transfection techniques. As used herein, the terms "transformation" "transduction", "infection" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In addition trasfection can be mediated by a transfection agent. By "transfection agent" is meant to include any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

Transfection may be "stable" (i.e. intergration of the foreign DNA into the host genome) or "transient" (i.e., DNA is episomally expressed in the host cells).

For stable transfection of mammalian cells, it is known that, depending upon the expression vector and transfection technique used, only a small fraction of cells may integrate the foreign DNA into their genome the remainder of the DNA remains episomal In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding or can be introduced on a separate vector. Cells stably transfected with the introduced nucleic acid can be identified by drug selection (e.g., cells that have incorporated the selectable marker gene will survive, while the other cells die). In another embodiment the cells modulated by the chimeric peptide or the transfected cells are identified by the induction of expression of a endogeneous reporter gene. In a specific embodiment, the promotor is the insulin promoter driving the expression of green flourescent protein (GFP).

Other advantages and characteristics of the invention will appear from the examples of embodiment that follow and refer to the attached drawings.

EXAMPLES

The invention is further illustrated in the following non-limiting examples.

Example 1

Synthesis of Chimeric Peptides and Diatos Peptide Vectors (DPVS)

Chemical Synthesis:

Peptide synthesis is done by techniques known to a person skilled in the art (Altergen and Neosystem). They are used in solid phase on Fmoc resin. Cleaving is done with trifluoroacetic acid (TFA), and the peptides were purified on a semi-preparatory HPLC-CR C5 column and diluted with a 0.1% TFA solution and an acetonitrile gradient (10%–70%) in the TFA. The lyophilized peptides were dissolved in NaCl 0.15 M.

Molecular Construction Allowing Preparation of Proteins Containing the Peptides in the Invention:

Molecular biology techniques make it possible to construct plasmids which, once introduced into adequate cells, permit the synthesis of vectorized macromolecules.

Construction of Vectors for Expression of Recombinant Proteins:

FIG. 1 shows the preparation of vectors that permit the expression of recombinant proteins containing the peptide sequences in the invention. The prokaryotic vector pQE30 (Qiagen) permits the expression of genes in the form of fusion proteins (or recombinant proteins) with the sequence 6×His. This vector carries the origin of replication ColE1, the strong promoter of phage T5, which can be induced by IPTG, the gene for β-lactase giving resistance to ampicillin and a multiple cloning site at 3' of the sequence coding the label 6×His permitting the cloning of complementary DNA in phase with the 6×His sequence.

The complementary oligonucleotides of 63-mer:
PAV1U: (SEQ ID NO:49)
5'gatccgtaaaacgaggactaaaactacgacacgtacgaccacgagta-acacgaatggacgtaa 3'
PAV1L: (SEQ ID NO:50)

5' gatcttacgtccattcgtgttactcgtggtcgtacgtgtcgtagttttag-tcctcgttttacg-3' are hybridized. The DNA segment obtained has a BamHI site at 5' and a BglII site at 3'. It codes for the peptide sequence PAV1: VKRGLKLRHVRPRVTRMDV (SEQ ID NO:51). This fragment is cloned at the BamHI site of vector pQE30. The complementary DNA (DNAc) coding for the Zebra viral protein (BZLF1) of the Epstein-Barr virus (EBV) or the Zebra protein deleted from its nuclear localization site (nls) of 35 amino acids were obtained by PCR. They were cloned at the BamHI site of the vector His-PAV1 or pQE30. The resultant plasmids permit the expression of recombinant proteins $His_6$-Zebra-PAV1, $His_6$-ZebraΔnls-PAV1, $His_6$-Zebra and $His_6$-ZebraΔnls after transformation of the E. coli bacteria.

Induction, Extraction and Purification of Recombinant Proteins:

The production of recombinant proteins is induced at 37° C. by the addition of 1 mM of IPTG (isopropyl-β-D-thiogalactopyranoside) to the bacterial cultures in exponential growth phase in Luria Bertani medium supplemented with 40 μg/ml of ampicillin. 12 hours after adding IPTG, the bacteria are centrifuged at 5700 g for 15 min. at 4° C. The bacterial residue is put in 5 volumes of denatured lysis buffer (20 mM Tris-HCl pH 7.8; 0.5 M NaCl; 10% glycerol; 6 M guanidine-HCl). After 20 min. of incubation at ambient temperature with slow mixing, the lysate is clarified by centrifuging it for 30 min. at 15000 g at 4° C. The supernatant containing the recombinant protein is stored at –80° C.

The 6×His recombinant proteins are purified by affinity chromatography on a "TALON" resin column (CLONTECH) pre-calibrated with denatured lysis buffer. After 3 successive washings of resin with 10 volumes of denatured lysis buffer containing 10 mM imidazole, the recombinant protein bonded to the column is renatured by a gradient of 6 to 0 M of guanidine-HCl in buffer 20 mM Tris-HCl pH7.8; 0.5 M NaCl; 10% glycerol; 0.5 mM PMSF. The recombinant protein is eluted with a gradient of 20 mM at 1 M of imidazole pH 8.0. The different eluates are analyzed on 12% SDS-acrylamide denatured gel. The fractions containing the purified protein are collected and dialyzed for 2 hours at 4° C. against the buffer 20 mM HEPES pH 7.5, 150 mM NaCl. The protein is concentrated, aliquoted and quick frozen in liquid nitrogen and stored at –80° C.

Peptides Used:

Non-Functionalized Peptides:

SEQ ID NO: 1. Peptide reacting with heparin that comes from the amino acid sequence (3358–3372) of the human lipoprotein B, Cardin et al., Biochem. Biophys. Res. Com. 154:741 (1988), also called DPV1.

SEQ ID NO: 2. Peptide reacting with the heparin dimer of SEQ ID NO: 1, also called $(DPV1)_2$.

SEQ ID NO: 3. Peptide reacting with the heparin trimer of SEQ ID NO: 1, also called $(DPV1)_3$.

SEQ ID NO: 4. Peptide corresponding to the hypervariable area CD3 of the anti-DNA monoclonal murine antibody F4.1 (Avrameas et al., Proc. Natl. Acad. Sci. 95:5601 (1998)).

SEQ ID NO: 5 Peptide containing SEQ ID NO: 1 and SEQ ID NO: 4.

SEQ ID NO: 6. Peptide containing part of CDR2 and CDR3 regions of monoclonal murine antibody F4.1 (Avrameas et al., Proc. Natl. Acad. Sci. 95:5601 (1998)).

SEQ ID NO: 7. Peptide containing SEQ ID NO: 1 and SEQ ID NO: 6.

SEQ ID NO: 8. Peptide corresponding to the hypervariable CD3 region of human anti-DNA monoclonal antibody RTT79 (Stevenson et al., J. Autoimmunity 6:809 (1993)).

SEQ ID NO: 9. Peptide containing SEQ ID NO: 1 and SEQ ID NO: 8.

SEQ ID NO: 10. Peptide reacting with heparin and containing SEQ ID NO: 1 and the sequence of the peptide corresponding to the hypervariable area CDR3 of the human anti-DNA monoclonal antibody NE-1 (Hirabayashi et al., Scand. J. Immunol. 37:533 (1993)), also called No. 1047.

SEQ ID NO: 11. Peptide containing SEQ ID NO: 1 and the sequence of the peptide corresponding to the hypervariable area CDR3 of the human anti-DNA monoclonal antibody RT72 (Kalsi et al., Lupus 4:375 (1995)).

SEQ ID NO: 12. Peptide containing the sequence of the NLS (nuclear localization signal) of cells 3T3 and SEQ ID NO: 6.

SEQ ID NO: 13. Peptide containing SEQ ID NO: 1 and the sequence from CDR2 and CDR3 regions of the anti-DNA human monoclonal antibody NE-1.

SEQ ID NO: 14. Peptide containing part of CDR3 region of murine monoclonal antibody F4.1 and SEQ ID NO: 6.

SEQ ID NO: 15. Peptide containing twice the sequence of the peptide corresponding to the hypervariable CDR3 region of the anti-DNA human monoclonal antibody NE-1.

SEQ ID NO: 16. Peptide resulting from the inclusion, in position 13–19, of SEQ ID NO: 1 in SEQ ID NO: 15.

SEQ ID NO: 17. Peptide reacting with heparin derived from the amino acid sequence of the human lipoprotein E (Cardin et al., Biochem. Biosphys. Res. Com. 154:741 (1988)), also called DPV4.

SEQ ID NO: 18. Peptide reacting with heparin derived from the amino acid sequence of agrine (Campanelli et al., Development 122:1663–1672 (1996)), protein of the extracellular matrix that regulates differentiation of the neuromuscular junction.

SEQ ID NO: 19. Dimer of SEQ ID NO: 18.

SEQ ID NO: 20. Peptide reacting with heparin derived from the amino acid sequence of insulin growth factor binding protein, also called DPV2 (Fowlkes et al., Endocrinol. 138:2280–2285 (1997)).

SEQ ID NO: 21. Peptide reacting with heparin and derived from the amino acid sequence of the C-terminal part of chain A of the platelet growth factor (Maher et al., Mol. Cell. Biol. 9:2251–2253 (1989)), also called DPV6.

SEQ ID NO: 22. Peptide containing 12 lysines (K) and SEQ ID NO: 6.

SEQ ID NO: 23. Peptide containing 12 lysines (K) and SEQ ID NO: 5.

SEQ ID NO: 24. Peptide having anti-microbial activity (Javadpour et al., J. Med. Chem. 39:3107–3113 (1996)).

SEQ ID NO: 25. Peptide reacting with heparin and corresponding to the sequence of the insulin-like growth factor-binding protein (Fowlkes et al., Endocrinol. 138:2280–2285 (1997)).

SEQ ID NO: 26. Peptide reacting with heparin and dimer of a peptide derived from the C-terminal part of the sequence of human dismutase superoxide (Inoue et al., FEBS 269:89–92 (1990)), also called $(DPV3)_2$.

SEQ ID NO: 27. Peptide reacting with heparin and corresponding to the sequence SEQ ID NO: 26 in which the amino acids are in configuration D.

SEQ ID NO: 28. Peptide reacting with heparin whose sequence is derived from SEQ ID NO: 26 and contains motif RGD selectively binding the αv integrins (21).

SEQ ID NO: 29. Peptide reacting with heparin and composed of peptides from SEQ ID NO: 1 and SEQ ID NO: 17, also called DPV1–DPV4.

SEQ ID NO: 30. Peptide reacting with heparin and derived from the C-terminal part of the sequence of the epidermal growth factor (EGF) (Arkonac et al., J. Biol. Chem. 273:4400–4405 (1998)), also called DPV7.

SEQ ID NO: 31. Peptide reacting with heparin and corresponding to the peptide whose sequence is SEQ ID NO: 12 where the amino acids are in front-back position.

SEQ ID NO: 32. Peptide reacting with heparin and corresponding to sequence SEQ ID NO: 30 in which the amino acids are in configuration D.

SEQ ID NO: 33. Peptide reacting with heparin and containing part of the sequence of the acid fibroblasts growth factor (aFGF) (Fromm et al., Arch. Biochem. Bioph. 343:92 (1997)), also called DPV8.

SEQ ID NO: 34. Peptide reacting with heparin and containing part of the sequence of the basic fibroblast growth factor (bFGF), also called DPV9 (Yayon et al., Cell 64:841–848 (1991)).

SEQ ID NO: 35. Peptide reacting with heparin and corresponding to a C-terminal part of the intestinal murine sequence (Gongqiao et al., Glyconjug J. 13:81–90 (1996)), also called DPV10.

SEQ ID NO: 36: Peptide reacting with heparin and containing part of the C-terminal sequence of human γ interferon (Lortat-Jacob & Grimaud, FEBS 280:152–154 (1991)), also called DPV11.

SEQ ID NO: 37: Peptide reacting with heparin and containing part of the sequence of subunit p40 of human interleukin 12 (Hasan et al., J. Immunol. 162:1064–1070 (1999)), also called DPV12.

SEQ ID NO: 38: Peptide reacting with heparin and containing part of the sequence of factor 1α derived from stromal cells (Amara et al., J. Biol. Chem. 272:200–204 (1999)), also called DPV13.

SEQ ID NO: 39: Peptide reacting with heparin and containing part of the sequence of the "heparin binding protein" (CAP 37) (Pohl et al., FEBS 272:200–204 (1990)), also called DPV15.

SEQ ID NO: 40: Peptide reacting with heparin corresponding to the peptide in sequence SEQ ID NO: 10 (1047) plus 13 N-terminal lysines.

SEQ ID NO: 41: Peptide reacting with heparin corresponding to the peptide in sequence SEQ ID NO: 28 $(DPV3)_2$) plus 13 N-terminal lysines.

SEQ ID NO: 42: Peptide reacting with heparin corresponding to the peptide in sequence SEQ ID NO: 39 (DPV10) plus 13 N-terminal lysines.

SEQ ID NO: 43: Peptide with anti-microbial activity containing peptides in sequences SEQ ID NO: 10 (1047) and SEQ ID NO: 24.

SEQ ID NO: 44: Peptide with anti-microbial activity containing peptides in sequences SEQ ID NO: 24 and SEQ ID NO: 30 (DPV7).

SEQ ID NO: 45: Peptide with anti-microbial activity containing peptides in sequences SEQ ID NO: 24 and SEQ ID NO: 38 (DPV13).

SEQ ID NO: 46: Peptide containing the peptide in sequence SEQ ID NO: 26 $(DPV3)_2$ plus glycine-phthalcyl in N-terminal.

SEQ ID NO: 47: Peptide containing the peptide in sequence SEQ ID NO: 21 (DPV6) plus a salicylyl motif in N-terminal.

SEQ ID NO: 48: Peptide containing the peptide in sequence SEQ ID NO: 21 (DPV6) plus a salicylic motif in C-terminal.

Functionalized Peptides:

These peptides correspond to SEQ ID NO: 1 to 48 above, but carry, on the N-terminal side, either a cysteine that allows covalent coupling to some substances of interest or biotin allowing non-covalent combination of peptides with streptavidin or avidin conjugated with peroxidase.

Example 2

Integrity of the CACO-2 Barrier Model

Caco-2 cells were seeded at a density of 160000 cells/cm$^2$ on a polyethylene terephtalate microporous membranes, previously coated with bovine dermal collagen, in a synthetic serum-free medium (Basal Defined Medium, BDM). Culture medium was changed three times a week and cells were maintained at 37° C. in a an atmosphere of 5% $CO_2$ for 18 days. As a negative control to check the integrity of the Caco-2 barrier, $10^6$ dpm/ml D-[$^{14}$C]-mannitol was used. As a positive control, L-[$^3$H]-proline was used: active transport $10^6$ dpm/ml, 10 µM as final concentration. Other controls included D-[$^{14}$C]-mannitol/L-[$^3$H]-Proline+DPV7 30 µg/ml and D-[$^{14}$C]-mannitol/L-[$^3$H]-proline+DPV10 30 µg/ml.

Trans-epithelial transport experiments were carried out. The trans-epithelial electrical resistance (TEER) was measured to check the integrity of the Caco-2 cell monolayers. The cell monolayers were preincubated in Hanks' balanced salt solution (HBSS, 5 mM glucose, supplemented with 10 mM Hepes) for 8 hours at 37° C. At 1, 2, 4 and 8 hours, 100 µl of medium was collected from the lower compartment and replaced by fresh HBSS. At the end of the experiment (8 hours), the cell monolayers were washed three times with PBS and TEER was measured. The cells were then collected in 400 µl of Tris-HCl 0.1 M pH 8.0, 0.5% Triton X100 and disrupted by ultrasonication. The radioactivity contained in 100 µL of cell homogenate was measured. The amount of radioactive material was analyzed by liquid scintillation spectrometry using a Packard Tri-carb 1600CA instrument (Packard Instrument company, Meriden, Conn., USA) after light dispersion in 2 ml of Aqualuma coktail (Lumac/3M by, Schaesberg, the Netherlands).

Figure 2:
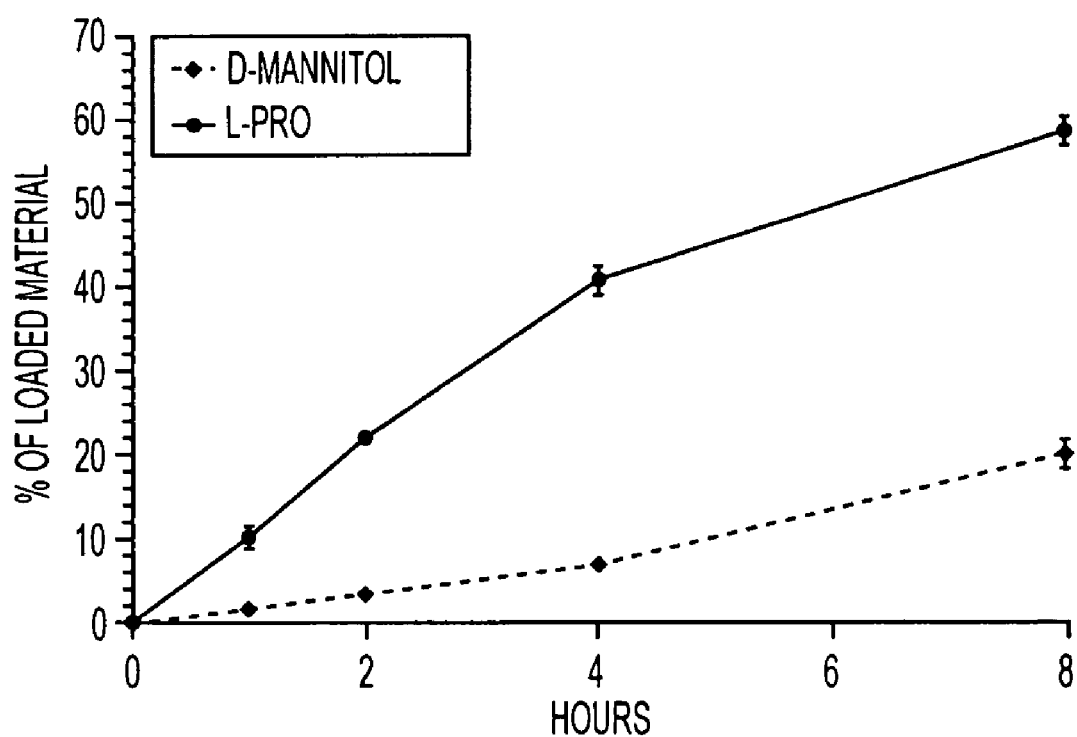
FIG. 2 is a line graph showing kinetics of the transport of D-[$^{14}$C]-mannitol and L-[$^3$H]proline.

FIG. 2 shows the transport of D-[$^{14}$C]-mannitol and L-[$^3$H]-proline. The results indicate that the trans-epithelial transport of D-[$^{14}$C]-mannitol and L-[$^3$H]-proline is proportional to the duration of the experiment during the first 4 hours. The transport of L-[3H]-proline (positive control) was higher than that of D-[$^{14}$C]-mannitol (negative control), indicating that the Caco-2 intestinal barrier model could be used to estimate the transport of the DPV-insulin compounds. Between 4 and 8 hours of incubation, the transport of L-[$^3$H]-proline slowed down and the transport of D-[$^{14}$C]-mannitol significantly increased. This observation resulted from an alteration of the cell monolayers by the long incubation in HBSS. A drastic decrease in TEER values measured at the end of the transport experiment (after 8 hours of incubation in HBSS) is in correlation with these observations (Table 1).

Figure 3A:
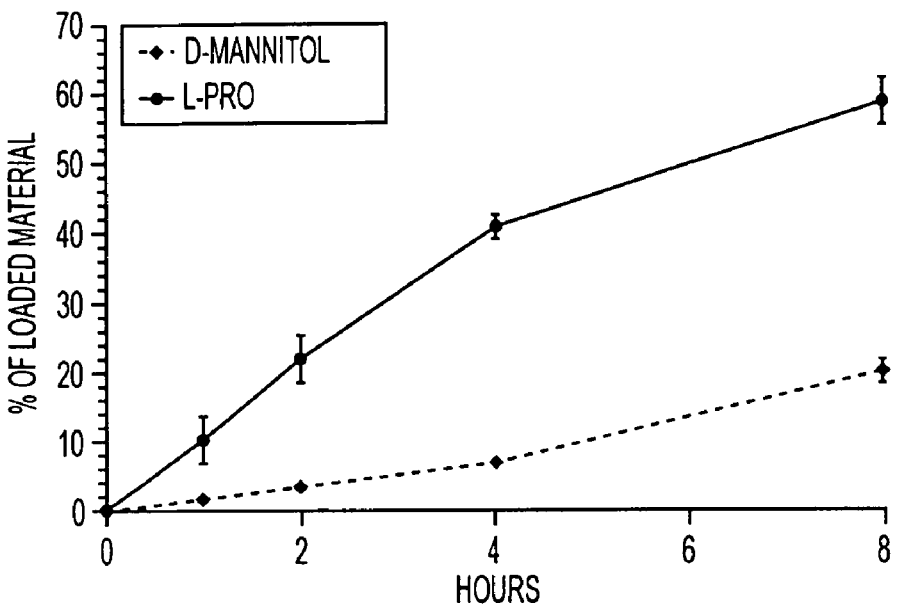
FIG. 3 is a line graph showing kinetics of the transport of D-[$^{14}$C]-mannitol and L-[$^3$H]pr in the presence of 30 μg/ml of DVP7-insulin (A) or DPV10-insulin (B).
Figure 3B:
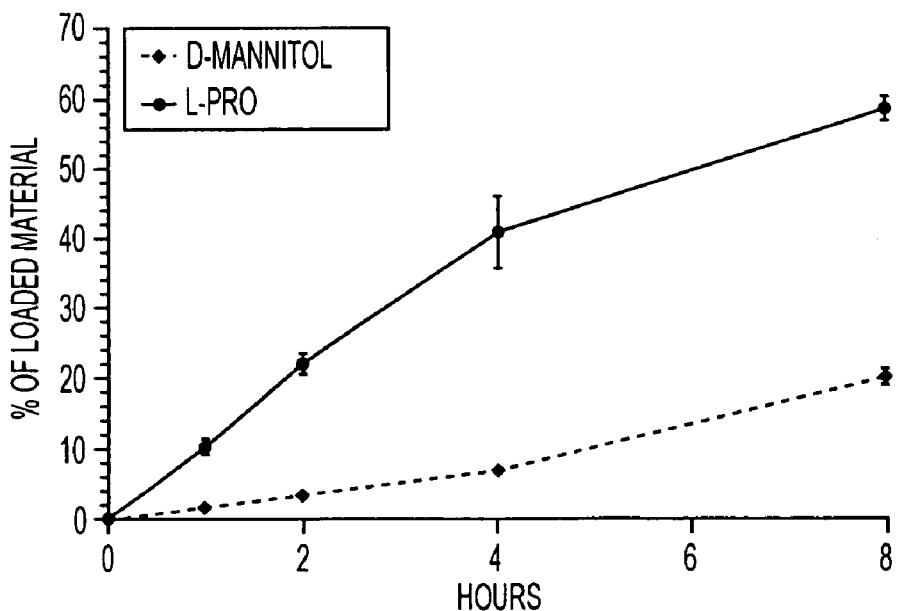
Figure 4:
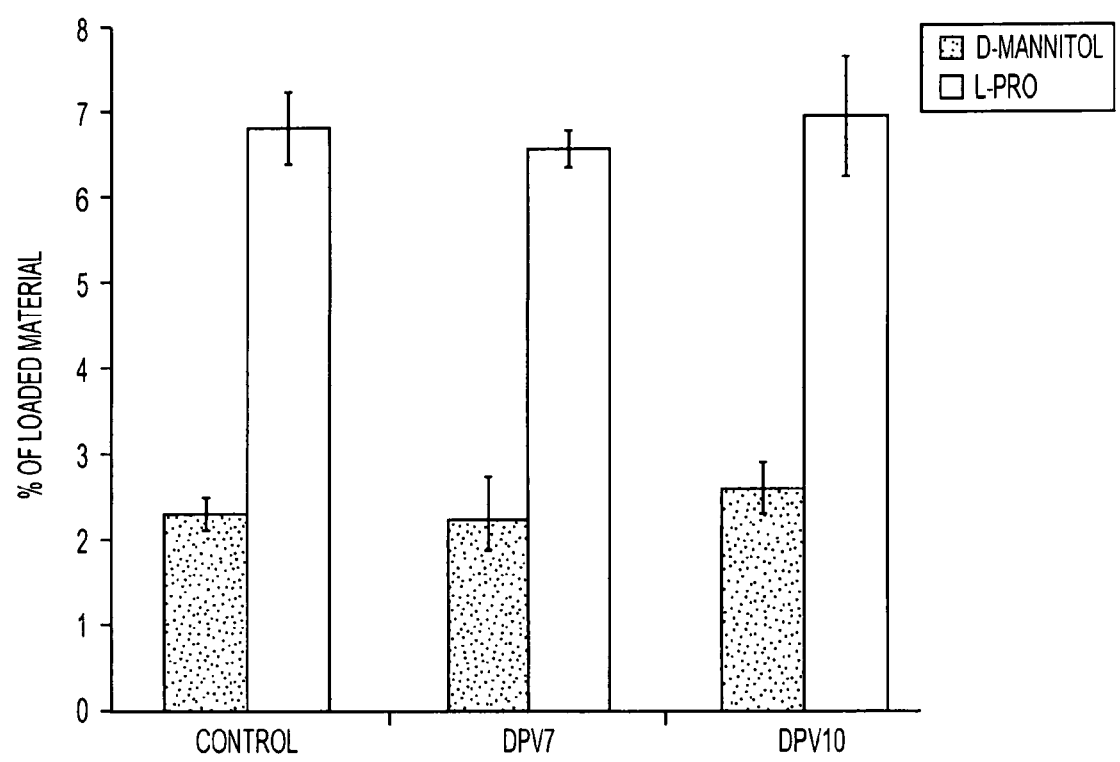
FIG. 4 is a bar graph showing D-[$^{14}$C]-mannitol and L[$^3$H]proline associated with the cells at 8 hours postincubation when they were incubated alone (control) or in the presence of 30 μg/ml of DVP7 or DVP10.

The presence of 30 µg/ml of DPV7 or DPV10 did not affect the transport of D-[$^{14}$C]-mannitol or L-[$^3$H]-proline (FIG. 3), nor the amounts of D-[$^{14}$C]-mannitol and L-[$^3$H]-proline associated with the cells at the end of the experiment (FIG. 4).

TABLE 1

TEER Measurements

| | Insert n° | TEER before incubation ($\Omega \cdot cm^2$) | TEER after incubation ($\Omega \cdot cm^2$) |
|---|---|---|---|
| Control | 1 | 540 | 143 |
| | 2 | 495 | 173 |
| | 3 | 512 | 124 |
| DPV7 | 1 | 506 | 117 |
| | 2 | 828 | 145 |
| | 3 | 545 | 129 |
| DPV10 | 1 | 500 | 153 |
| | 2 | 458 | 201 |
| | 3 | 501 | 201 |

Example 3

Insulin and DPV-Insulin Conjugates Trans-Epithelial Transport

DPV-insulin conjugates were synthesized. Briefly, insulin was activated by a 10 molar excess of a hetero-bifunctionnal cross-linking agent, SMCC. After several washing steps, DPV7 or DPV10 was added in a 5 fold molar excess. The samples were washed again to eliminate uncoupled materials, and the conjugates were checked by SDS-Page electrophoresis analysis. Insulin, DPV7-insulin, and DPV10-insulin were diluted in NaCl 0.15 M to obtain a final concentration of 0.65 mg/ml. 30 µg of each molecule was incubated on the Caco-2 cell monolayers.

Trans-epithelial transport experiments were carried out. The trans-epithelial electrical resistance (TEER) was measured to check the integrity of the Caco-2 cell monolayers. The cell monolayers were preincubated in Hanks' balanced salt solution (HBSS, 5 mM glucose, supplemented with 10 mM Hepes) for 30 minutes at 37° C. The insulin compounds were added at a concentration of 60 µg/ml in 0.5 ml of HBSS medium in the upper compartment of the insert, facing the apical side of the cells. The upper and lower compartment contained 0.5 and 1.25 ml of HBSS respectively. The cell monolayers were incubated at 37° C. for 1, 4 or 8 hours with insulin compounds. The media of the upper and lower compartments were collected. The cell monolayers were washed three times with PBS and TEER was measured. The cells were collected in 400 µl of Tris-HCl 0.1 M pH 8.0, 0.5% Triton X100. For each condition, three inserts were used (triplicates).

Table 2 shows the values of TEER measured before and after incubation with the compounds. The results indicate that DPV7-insulin induced a significant decrease in TEER after 1 and 4 hours of incubation, indicating that the integrity of the Caco-2 cell monolayer was affected by DPV7-insulin at these two time points. This TEER breakdown and this change in the cell morphology were not observed for insulin and DPV10-insulin. The results also showed a significant decrease in TEER after 8 h of incubation with the three compounds. This is in agreement with the results from Example 1, indicating that a time of incubation in HBSS longer than 4 hours alters the Caco-2 cell barrier.

TABLE 2

TEER Measurements

| Insert n° | TEER before incubation ($\Omega \cdot cm^2$) | TEER after incubation ($\Omega \cdot cm^2$) |
|---|---|---|
| Insulin 1 h | 1 | 458 | 478 |
| | 2 | 592 | 561 |
| | 3 | 445 | 425 |
| Insulin 4 h | 1 | 510 | 305 |
| | 2 | 451 | 324 |
| | 3 | 606 | 325 |
| Insulin 8 h | 1 | 442 | 151 |
| | 2 | 451 | 145 |
| | 3 | 498 | 151 |
| DPV7-insulin 1 h | 1 | 515 | 143 |
| | 2 | 434 | 202 |
| | 3 | 542 | 178 |
| DPV7-insulin 4 h | 1 | 639 | 129 |
| | 2 | 548 | 112 |
| | 3 | 600 | 116 |
| DPV7-insulin 8 h | 1 | 543 | 123 |
| | 2 | 583 | 95 |
| | 3 | 473 | 112 |
| DPV10-insulin 10 h | 1 | 533 | 537 |
| | 2 | 656 | 660 |
| | 3 | 599 | 573 |
| DPV10-insulin 4 h | 1 | 678 | 553 |
| | 2 | 451 | 386 |
| | 3 | 498 | 416 |
| DPV10-insulin 8 h | 1 | 650 | 194 |
| | 2 | 613 | 190 |
| | 3 | 605 | 186 |

Example 4

Detection and Quantification of Insulin Compounds

Free insulin concentrations were measured with an ELISA kit from Dako (ref. K6219). DPV-insulin conjugates were detected by a self-manufactured assay. Briefly, DPVinsulin conjugates were absorbed on heparin-coated wells in 96-well microtiter plates. The levels of DPV-insulin conjugates were quantified by an ELISA-derived assay using a mouse anti-insulin monoclonal antibody and peroxydase-coupled secondary antibody.

Figure 5:
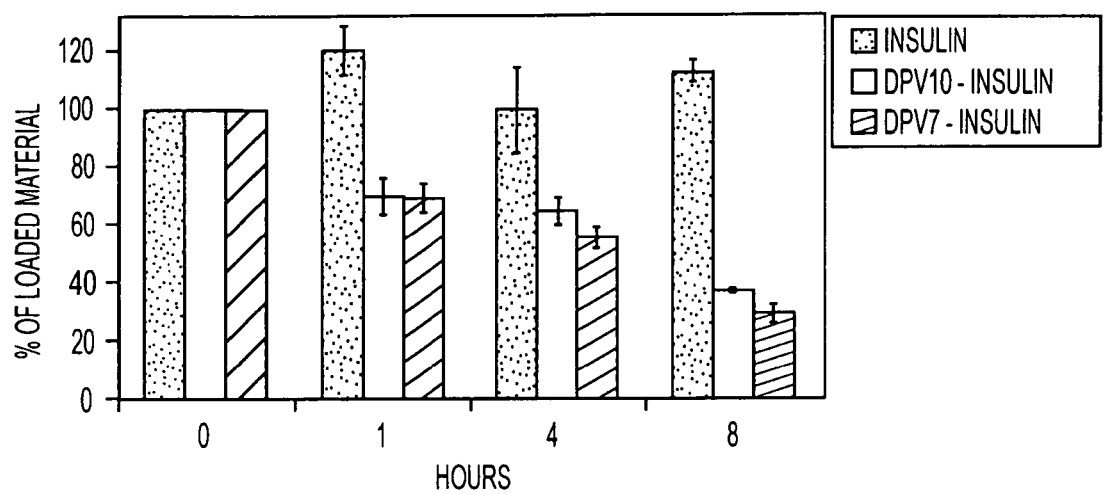
FIG. 5 is a bar graph showing levels of insulin and DPV-insulin conjugates in the apical medium.

The samples collected after incubation with the Caco-2 cells were transferred in BSA coated microtubes and stored at −20° C. until insulin levels were measured. Free insulin levels stayed stable in the apical medium during the whole experiment. In contrast, the apical concentration of DPV-insulin conjugates decreased as a function of the time. At 8 hours, the levels of DPV7-insulin and DPV10-insulin corresponded to 25% and 35% respectively of the initial loading (FIG. 5). Significant decreases in DPV-insulin conjugate levels were also observed at 1 and 4 hours (FIG. 5). At these two time points, the levels of DPV-insulin conjugates were 70% of the initial loading at 1 hour for both conjugates. 54% and 64% of the initial loading at 4 hours, for DPV7-insulin and DPV10-insulin respectively.

A small quantity of free insulin was detected in the basolateral medium, (0.2% of the loaded material). No significant amounts of DPV-insulin conjugates were detected in the basolateral medium, possibly because the assay for the detection of DPV-insulin conjugates is 1000 fold less sensitive than the Dako assay for the detection of free insulin. Taking this difference of sensitivity into account, it would have been unlikely to detect such a small quantity of DPV-insulin conjugate.

Figure 6:
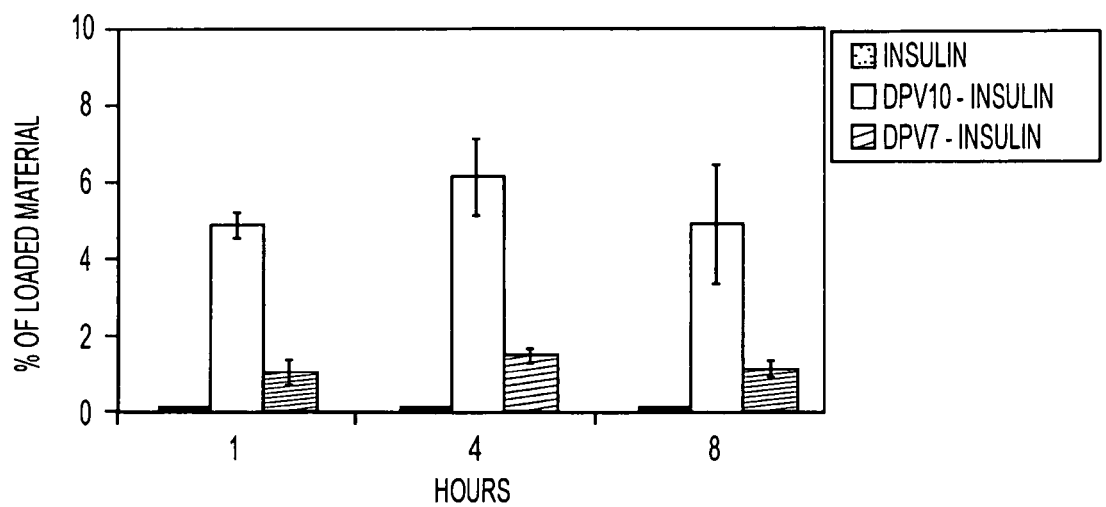
FIG. 6 is a bar graph showing levels of DPV-insulin conjugates in the cell lysates as a function of time.

A very small quantity of free insulin was found in the cell lysate, (approximately 0.004% of the initial loading). In contrast, the quantity of DPV7-insulin and DPV10-insulin detected in the cell lysate after one hour of transport reached 1% and 4% of the initial loading, respectively (FIG. 6). These levels were stable throughout the experiment, suggesting that the compounds did not accumulate intracellularly, and could exit the Caco-2 cells.

The filters on which Caco-2 cells were grown were also analysed for the presence of insulin and DPV-insulin conjugates. Free and DPV-insulin conjugates were detected on the filters using the same quantitation assay, allowing a direct comparison of the quantities of compounds that remained on the filters.

Results indicated that only a small amount of free insulin was remaining on the filters. In contrast, when coupled to DPV10 or DPV7, insulin conjugates clearly stayed trapped on the cell culture inserts.

Example 5

In Vitro Quantification of DPV-Insulin Conjugates

DPV-insulin conjugates were synthesized as described in Example 2. In order to validate the measurement of conjugate concentration, several tests are performed. Recognition of insulin-DPV conjugates is verified using an RIA test. A standard concentration curve is established in vitro for each conjugate, in parallel with free insulin, so as to make sure that the conjugates are recognized by the anti-insulin antibody as well as to determine whether the conjugates can be quantified with a correct sensibility using the RIA test.

Example 6

In Vivo Quantification of DPV-Insulin Conjugates

DPV-insulin conjugates were synthesized as described in Example 2. The activity of DPV-insulin conjugates are assessed in vivo, after a subcutaneous injection of appropriate levels of conjugates in hyperglycemic rats. Controls are injected with either free insulin or NaCl. Blood samples are collected at predetermined time points and analyzed for both insulin and glucose concentrations, using an ELISA and glucose oxidase method, respectively. An increase in blood insulin concentration and a subsequent decrease in blood glucose levels indicates that the DPV-insulin conjugates are biologically active.

Example 7

In Vivo Evaluation of DPV-Insulin Conjugates after Oral Administration

In order to assess the passage of the intestinal barrier by the DPV-insulin conjugates, compounds are inserted into the ileal lumen of hyperglycemic rats. Controls are administered with either free insulin or NaCl, before evaluation of the passage of insulin in the blood of the treated rats.

Glycemia is controlled for all animals every 15 minutes for at least three hours following administration, then every hour for the following 12 hours. Blood samples are collected at predetermined time points and analyzed for glucose concentrations using a glucose oxidase method. A decrease in blood glucose levels indicates the passage of insulin through the intestinal barrier.

For those animals in which the in vivo tests indicate no biological activity of insulin however, in vitro quantification was possible using the RIA test, blood is taken from all rats at one time point after the subcutaneous injection and the level of insulin conjugate is determined by RIA in each blood sample. This direct detection of the insulin allows for the determination whether the conjugate has crossed the intestinal barrier.

Example 8

Morphological and Immunocytochemical Studies

Small intestinal ileal tissue of the hyperglycemic rats contacted with the DPV-insulin conjugates is collected in order to verify the integrity of the tight junctions. An immunocytochemical study is performed after a single time point (30 or 60 minutes) to demonstrate transcellular transport of insulin.

What is claimed is:

1. A chimeric peptide comprising a first domain and a second domain, wherein the first domain comprises the translocation sequence of SEQ ID NO:35 which facilitates active transport across a biological membrane and the second domain comprises at least a biologically active portion of an insulin polypeptide.

2. The peptide of claim 1, wherein the translocation sequence binds an aminoglycan.

3. The peptide of claim 2, wherein the aminoglycan is heparin or chondroitin sulfate.

4. The peptide of claim 1, wherein the chimeric peptide translocates a physiological barrier.

5. The peptide of claim 4, wherein the physiological barrier is the gastrointestinal barrier or the blood-brain barrier.

6. The peptide of claim 1, further comprising a third domain selected from the group consisting of:
   (a) a CDR3 region of a human anti-DNA antibody;
   (b) a CDR2 region of a human anti-DNA antibody;
   (c) a CDR3 region of a murine anti-DNA antibody; and
   (d) a CDR2 region of a murine anti-DNA antibody.

7. A composition comprising a peptide according to claims 1 or 6 and a pharmaceutically acceptable diluent, carrier or adjuvant.

8. The composition according to claim 7 in a formulation suitable for oral administration.

9. A kit comprising in one or more containers, the composition of claim 7.

10. A method of treating diabetes in a subject, comprising administering to the subject the composition of claim 1.

11. A method of increasing the intracellular concentration of insulin in a eukaryotic cell, the method comprising:
   (a) providing the peptide of claim 1; and
   (b) contacting the cell with the peptide under conditions promoting active metabolism of the eukaryotic cell.

12. A method of decreasing the intracellular concentration of glucose in a eukaryotic cell, the method comprising:
   (a) providing the peptide of claim 1; and
   (b) contacting the cell with the peptide under conditions promoting active metabolism of the eukaryotic cell.

13. A method of increasing the serum insulin concentration in a subject, comprising administering to the subject the peptide of claim 1.

14. A method of decreasing the serum glucose concentration in a subject, comprising administering to the subject the peptide of claim 1.

15. The chimeric peptide of claim 1, wherein the second domain comprising at least a biologically active portion of an insulin polypeptide still has at least one function of native insulin.

16. The chimeric peptide of claim 15, wherein the at least one function of native insulin is decreasing blood glucose levels.

* * * * *

SEQUENCE LISTING

<160> NUMBER OF SEQ ID NOS: 56

<210> SEQ ID NO 1
<211> LENGTH: 7
<212> TYPE: PRT
<213> ORGANISM: Homo sapiens

<400> SEQUENCE: 1

Val Lys Arg Gly Leu Lys Leu
1               5

<210> SEQ ID NO 2
<211> LENGTH: 14
<212> TYPE: PRT
<213> ORGANISM: Homo sapiens

<400> SEQUENCE: 2

Val Lys Arg Gly Leu Lys Leu Val Lys Arg Gly Leu Lys Leu
1               5                   10

<210> SEQ ID NO 3
<211> LENGTH: 21
<212> TYPE: PRT
<213> ORGANISM: Homo sapiens

<400> SEQUENCE: 3

Val Lys Arg Gly Leu Lys Leu Val Lys Arg Gly Leu Lys Leu Val Lys
1               5                   10                  15

Arg Gly Leu Lys Leu
            20

<210> SEQ ID NO 4
<211> LENGTH: 11
<212> TYPE: PRT
<213> ORGANISM: Mus musculus x Rattus norvegicus

<400> SEQUENCE: 4

Arg Gln Lys Tyr Asn Lys Arg Ala Met Asp Tyr
1               5                   10

<210> SEQ ID NO 5
<211> LENGTH: 18
<212> TYPE: PRT
<213> ORGANISM: Homo Sapiens-Mus musculus-Rattus norvegicus

<400> SEQUENCE: 5

Val Lys Arg Gly Leu Lys Leu Arg Gln Lys Tyr Asn Lys Arg Ala Met
1               5                   10                  15

Asp Tyr

```
<210> SEQ ID NO 6
<211> LENGTH: 20
<212> TYPE: PRT
<213> ORGANISM: Mus musculus x Rattus norvegicus

<400> SEQUENCE: 6

Thr Tyr Tyr Ser Asp Thr Val Lys Gly Arg Phe Thr Arg Gln Lys Tyr
 1               5                  10                  15

Asn Lys Arg Ala
            20

<210> SEQ ID NO 7
<211> LENGTH: 26
<212> TYPE: PRT
<213> ORGANISM: Homo Sapien-Mus musculus-Rattus norvegicus

<400> SEQUENCE: 7

Val Lys Arg Gly Leu Lys Leu Thr Tyr Tyr Ser Asp Thr Val Lys Gly
 1               5                  10                  15

Arg Phe Thr Arg Gln Tyr Asn Lys Arg Ala
            20                  25

<210> SEQ ID NO 8
<211> LENGTH: 17
<212> TYPE: PRT
<213> ORGANISM: Homo sapiens

<400> SEQUENCE: 8

Val Arg Arg Ser Gly Arg Val Val Pro Ala Ala Pro Arg Asn Arg
 1               5                  10                  15

Asp

<210> SEQ ID NO 9
<211> LENGTH: 24
<212> TYPE: PRT
<213> ORGANISM: Homo sapiens

<400> SEQUENCE: 9

Val Lys Arg Gly Leu Lys Leu Val Arg Arg Ser Gly Arg Val Val Val
 1               5                  10                  15

Pro Ala Ala Pro Arg Asn Arg Asp
            20

<210> SEQ ID NO 10
<211> LENGTH: 19
<212> TYPE: PRT
<213> ORGANISM: Homo sapiens

<400> SEQUENCE: 10

Val Lys Arg Gly Leu Lys Leu Arg His Val Arg Pro Arg Val Thr Arg
 1               5                  10                  15

Met Asp Val

<210> SEQ ID NO 11
<211> LENGTH: 19
<212> TYPE: PRT
<213> ORGANISM: Homo sapiens

<400> SEQUENCE: 11

Val Lys Arg Gly Leu Lys Leu Gly Tyr Tyr Asp Phe Trp Ser Gly Pro
 1               5                  10                  15

Gly Lys Asn
```

-continued

<210> SEQ ID NO 12
<211> LENGTH: 27
<212> TYPE: PRT
<213> ORGANISM: Mus musculus x Rattus norvegicus

<400> SEQUENCE: 12

Asn Val Lys Lys Pro Lys Leu Thr Tyr Tyr Ser Asp Thr Val Lys Gly
1               5                   10                  15

Arg Phe Thr Arg Gln Lys Tyr Asn Lys Arg Ala
            20                  25

<210> SEQ ID NO 13
<211> LENGTH: 31
<212> TYPE: PRT
<213> ORGANISM: Homo sapiens

<400> SEQUENCE: 13

Val Lys Arg Gly Leu Lys Leu Ser Gly Ser Thr Asn Tyr Asn Pro Ser
1               5                   10                  15

Leu Lys Ser Arg His Val Arg Pro Arg Val Thr Arg Met Asp Val
            20                  25                  30

<210> SEQ ID NO 14
<211> LENGTH: 28
<212> TYPE: PRT
<213> ORGANISM: Mus musculus x Rattus norvegicus

<400> SEQUENCE: 14

Arg Gln Lys Tyr Asn Lys Arg Ala Thr Tyr Tyr Ser Asp Thr Val Lys
1               5                   10                  15

Gly Arg Phe Thr Arg Gln Lys Tyr Asn Lys Arg Ala
            20                  25

<210> SEQ ID NO 15
<211> LENGTH: 24
<212> TYPE: PRT
<213> ORGANISM: Homo sapiens

<400> SEQUENCE: 15

Arg Gly Val Arg Pro Arg Val Thr Arg Met Asp Val Arg His Val Arg
1               5                   10                  15

Pro Arg Val Thr Arg Met Asp Val
            20

<210> SEQ ID NO 16
<211> LENGTH: 31
<212> TYPE: PRT
<213> ORGANISM: Homo sapiens

<400> SEQUENCE: 16

Arg His Val Arg Pro Arg Val Thr Arg Met Asp Val Val Lys Arg Gly
1               5                   10                  15

Leu Lys Leu Arg His Val Arg Pro Arg Val Thr Arg Met Asp Val
            20                  25                  30

<210> SEQ ID NO 17
<211> LENGTH: 8
<212> TYPE: PRT
<213> ORGANISM: Homo sapiens

<400> SEQUENCE: 17

```
Leu Arg Lys Arg Leu Leu Arg Asp
 1               5

<210> SEQ ID NO 18
<211> LENGTH: 4
<212> TYPE: PRT
<213> ORGANISM: Homo sapiens

<400> SEQUENCE: 18

Lys Ser Arg Lys
 1

<210> SEQ ID NO 19
<211> LENGTH: 8
<212> TYPE: PRT
<213> ORGANISM: Homo sapiens

<400> SEQUENCE: 19

Lys Ser Arg Lys Lys Ser Arg Lys
 1               5

<210> SEQ ID NO 20
<211> LENGTH: 12
<212> TYPE: PRT
<213> ORGANISM: Homo sapiens

<400> SEQUENCE: 20

Arg Lys Gly Phe Tyr Lys Arg Lys Gln Cys Lys Pro
 1               5                  10

<210> SEQ ID NO 21
<211> LENGTH: 17
<212> TYPE: PRT
<213> ORGANISM: Homo sapiens

<400> SEQUENCE: 21

Gly Arg Pro Arg Glu Ser Gly Lys Lys Arg Lys Arg Lys Arg Leu Lys
 1               5                  10                  15
Pro

<210> SEQ ID NO 22
<211> LENGTH: 32
<212> TYPE: PRT
<213> ORGANISM: Mus musculis x Rattus norvegicus

<400> SEQUENCE: 22

Lys Lys Lys Lys Lys Lys Lys Lys Lys Lys Lys Thr Tyr Tyr Ser
 1               5                  10                  15
Asp Thr Val Lys Gly Arg Phe Thr Arg Gln Lys Tyr Asn Lys Arg Ala
                20                  25                  30

<210> SEQ ID NO 23
<211> LENGTH: 30
<212> TYPE: PRT
<213> ORGANISM: Mus musculis x Rattus norvegicus

<400> SEQUENCE: 23

Lys Lys Lys Lys Lys Lys Lys Lys Lys Lys Lys Val Lys Arg Gly
 1               5                  10                  15
Leu Lys Leu Arg Gln Lys Tyr Asn Lys Arg Ala Met Asp Tyr
                20                  25                  30

<210> SEQ ID NO 24
```

```
<211> LENGTH: 14
<212> TYPE: PRT
<213> ORGANISM: Artificial Sequence
<220> FEATURE:
<223> OTHER INFORMATION: Description of Artificial Sequence: Peptide
      Having Anti-Microbial Activity

<400> SEQUENCE: 24

Lys Leu Ala Lys Leu Ala Lys Lys Leu Ala Lys Leu Ala Lys
 1               5                  10

<210> SEQ ID NO 25
<211> LENGTH: 18
<212> TYPE: PRT
<213> ORGANISM: Homo sapiens

<400> SEQUENCE: 25

Arg Lys Gly Lys Phe Tyr Lys Arg Lys Gln Cys Lys Pro Ser Arg Gly
 1               5                  10                  15

Arg Lys

<210> SEQ ID NO 26
<211> LENGTH: 18
<212> TYPE: PRT
<213> ORGANISM: Homo sapiens

<400> SEQUENCE: 26

Ser Glu Arg Lys Lys Arg Arg Arg Glu Ser Arg Lys Lys Arg Arg Arg
 1               5                  10                  15

Glu Ser

<210> SEQ ID NO 27
<211> LENGTH: 18
<212> TYPE: PRT
<213> ORGANISM: Homo sapiens
<220> FEATURE:
<221> NAME/KEY: VARIANT
<222> LOCATION: (1)..(18)
<223> OTHER INFORMATION: All amino acids are in configuration D

<400> SEQUENCE: 27

Ser Glu Arg Lys Lys Arg Arg Arg Glu Ser Arg Lys Lys Arg Arg Arg
 1               5                  10                  15

Glu Ser

<210> SEQ ID NO 28
<211> LENGTH: 16
<212> TYPE: PRT
<213> ORGANISM: Homo sapiens

<400> SEQUENCE: 28

Arg Lys Lys Arg Arg Arg Gly Asp Arg Lys Lys Arg Arg Arg Gly Asp
 1               5                  10                  15

<210> SEQ ID NO 29
<211> LENGTH: 15
<212> TYPE: PRT
<213> ORGANISM: Homo sapiens

<400> SEQUENCE: 29

Val Lys Arg Gly Leu Lys Leu Leu Arg Lys Arg Leu Leu Arg Asp
 1               5                  10                  15

<210> SEQ ID NO 30
```

```
<211> LENGTH: 15
<212> TYPE: PRT
<213> ORGANISM: Homo sapiens

<400> SEQUENCE: 30

Gly Lys Arg Lys Lys Lys Gly Lys Leu Gly Lys Lys Arg Asp Pro
 1               5                  10                  15

<210> SEQ ID NO 31
<211> LENGTH: 16
<212> TYPE: PRT
<213> ORGANISM: Homo sapiens
<220> FEATURE:
<221> NAME/KEY: VARIANT
<222> LOCATION: (1)..(16)
<223> OTHER INFORMATION: The amino acids are in front-back position

<400> SEQUENCE: 31

Pro Asp Arg Lys Lys Gly Leu Lys Gly Lys Lys Lys Arg Lys Lys Gly
 1               5                  10                  15

<210> SEQ ID NO 32
<211> LENGTH: 14
<212> TYPE: PRT
<213> ORGANISM: Homo sapiens
<220> FEATURE:
<221> NAME/KEY: VARIANT
<222> LOCATION: (1)..(14)
<223> OTHER INFORMATION: All amino acids are in configuration D

<400> SEQUENCE: 32

Gly Lys Arg Lys Lys Lys Gly Lys Leu Gly Lys Lys Arg Asp
 1               5                  10

<210> SEQ ID NO 33
<211> LENGTH: 13
<212> TYPE: PRT
<213> ORGANISM: Homo sapiens

<400> SEQUENCE: 33

Gly Leu Lys Lys Asn Gly Ser Cys Lys Arg Gly Pro Arg
 1               5                  10

<210> SEQ ID NO 34
<211> LENGTH: 15
<212> TYPE: PRT
<213> ORGANISM: Homo sapiens

<400> SEQUENCE: 34

Tyr Arg Ser Arg Lys Tyr Ser Ser Trp Tyr Tyr Ala Leu Lys Arg
 1               5                  10                  15

<210> SEQ ID NO 35
<211> LENGTH: 14
<212> TYPE: PRT
<213> ORGANISM: Homo sapiens

<400> SEQUENCE: 35

Ser Arg Arg Ala Arg Arg Ser Pro Arg His Leu Gly Ser Gly
 1               5                  10

<210> SEQ ID NO 36
<211> LENGTH: 10
<212> TYPE: PRT
<213> ORGANISM: Homo sapiens

<400> SEQUENCE: 36
```

```
Ala Lys Thr Gly Lys Arg Lys Arg Ser Gly
 1               5                  10
```

<210> SEQ ID NO 37
<211> LENGTH: 13
<212> TYPE: PRT
<213> ORGANISM: Homo sapiens

<400> SEQUENCE: 37

```
Gln Gly Lys Ser Lys Arg Glu Lys Lys Asp Arg Val Phe
 1               5                  10
```

<210> SEQ ID NO 38
<211> LENGTH: 12
<212> TYPE: PRT
<213> ORGANISM: Homo sapiens

<400> SEQUENCE: 38

```
Lys His Leu Lys Lys His Leu Lys Lys His Leu Lys
 1               5                  10
```

<210> SEQ ID NO 39
<211> LENGTH: 17
<212> TYPE: PRT
<213> ORGANISM: Homo sapiens

<400> SEQUENCE: 39

```
Leu Arg Arg Glu Arg Gln Ser Arg Leu Arg Arg Glu Arg Ser Gln Ser
 1               5                  10                  15

Arg
```

<210> SEQ ID NO 40
<211> LENGTH: 32
<212> TYPE: PRT
<213> ORGANISM: Homo sapiens

<400> SEQUENCE: 40

```
Lys Lys Lys Lys Lys Lys Lys Lys Lys Lys Lys Lys Lys Val Lys Arg
 1               5                  10                  15

Gly Leu Lys Leu Arg His Val Arg Pro Arg Val Thr Arg Met Asp Val
                20                  25                  30
```

<210> SEQ ID NO 41
<211> LENGTH: 31
<212> TYPE: PRT
<213> ORGANISM: Homo sapiens

<400> SEQUENCE: 41

```
Lys Lys Lys Lys Lys Lys Lys Lys Lys Lys Lys Lys Lys Ser Glu Arg
 1               5                  10                  15

Lys Lys Arg Arg Arg Glu Ser Arg Lys Lys Arg Arg Arg Glu Ser
                20                  25                  30
```

<210> SEQ ID NO 42
<211> LENGTH: 27
<212> TYPE: PRT
<213> ORGANISM: Homo sapiens

<400> SEQUENCE: 42

```
Lys Lys Lys Lys Lys Lys Lys Lys Lys Lys Lys Lys Lys Ser Arg Arg
 1               5                  10                  15

Ala Arg Arg Ser Pro Arg His Leu Gly Ser Gly
```

-continued

```
                20                  25

<210> SEQ ID NO 43
<211> LENGTH: 21
<212> TYPE: PRT
<213> ORGANISM: Homo sapiens

<400> SEQUENCE: 43

Val Lys Arg Gly Leu Lys Leu Lys Leu Ala Lys Leu Ala Lys Lys Leu
1               5                   10                  15

Ala Lys Leu Ala Lys
            20

<210> SEQ ID NO 44
<211> LENGTH: 29
<212> TYPE: PRT
<213> ORGANISM: Homo sapiens

<400> SEQUENCE: 44

Lys Leu Ala Lys Leu Ala Lys Leu Ala Lys Leu Ala Lys Gly Lys
1               5                   10                  15

Arg Lys Lys Lys Gly Lys Leu Gly Lys Lys Arg Asp Pro
            20                  25

<210> SEQ ID NO 45
<211> LENGTH: 26
<212> TYPE: PRT
<213> ORGANISM: Homo sapiens

<400> SEQUENCE: 45

Lys Leu Ala Lys Leu Ala Lys Lys Leu Ala Lys Leu Ala Lys Lys His
1               5                   10                  15

Leu Lys Lys His Leu Lys Lys His Leu Lys
            20                  25

<210> SEQ ID NO 46
<211> LENGTH: 18
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Residue of glycine-phthaloyl in N-terminal
      position (Xaa)

<400> SEQUENCE: 46

Xaa Gly Arg Lys Lys Arg Arg Arg Glu Ser Arg Lys Lys Arg Arg Arg
1               5                   10                  15

Glu Ser

<210> SEQ ID NO 47
<211> LENGTH: 18
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Has a salicylic motif (named Xaa) in N-terminal
      position.

<400> SEQUENCE: 47

Xaa Gly Arg Pro Arg Glu Ser Gly Lys Lys Arg Lys Arg Lys Arg Leu
1               5                   10                  15

Lys Pro
```

```
<210> SEQ ID NO 48
<211> LENGTH: 19
<212> TYPE: PRT
<213> ORGANISM: Homo sapiens
<220> FEATURE:
<221> NAME/KEY: VARIANT
<222> LOCATION: (17)...(17)
<223> OTHER INFORMATION: Has a salicylic motif (named X) in C-terminal
      position

<400> SEQUENCE: 48

Gly Arg Pro Arg Glu Ser Gly Lys Lys Arg Lys Arg Lys Arg Leu Lys
 1               5                  10                  15

Xaa Pro Gly

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence:PAV1U PCR
      Primer

<400> SEQUENCE: 49
gatccgtaaa acgaggacta aaactacgac acgtacgacc acgagtaaca cgaatggacg      60
taa                                                                   63

<210> SEQ ID NO 50
<211> LENGTH: 63
<212> TYPE: DNA
<213> ORGANISM: Artificial Sequence
<220> FEATURE:
<223> OTHER INFORMATION: Description of Artificial Sequence:PAV1L PCR
      Primer

<400> SEQUENCE: 50
gatcttacgt ccattcgtgt tactcgtggt cgtacgtgtc gtagttttag tcctcgtttt      60
acg                                                                   63

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence:PAV1 Peptide
      Sequence

<400> SEQUENCE: 51

Val Lys Arg Gly Leu Lys Leu Arg His Val Arg Pro Arg Val Thr Arg
 1               5                  10                  15

Met Asp Val

<210> SEQ ID NO 52
<211> LENGTH: 51
<212> TYPE: PRT
<213> ORGANISM: Homo sapiens

<400> SEQUENCE: 52

Gly Ile Val Glu Gln Cys Cys Thr Ser Ile Cys Ser Leu Tyr Gln
 1               5                  10                  15

Leu Glu Asn Tyr Cys Asn Phe Val Asn Gln His Leu Cys Gly Ser
                20                  25                  30
```

-continued

His Leu Val Glu Ala Leu Tyr Leu Val Cys Gly Glu Arg Gly Phe
                35                  40                  45

Phe Tyr Thr Pro Lys Thr
                50

<210> SEQ ID NO 53
<211> LENGTH: 51
<212> TYPE: PRT
<213> ORGANISM: Homo sapiens

<400> SEQUENCE: 53

Gly Ile Val Glu Gln Cys Cys Thr Ser Ile Cys Ser Leu Tyr Gln
 1               5                  10                  15

Leu Glu Asn Tyr Cys Asn Phe Val Asn Gln His Leu Cys Gly Ser
                20                  25                  30

His Leu Val Glu Ala Leu Tyr Leu Val Cys Gly Glu Arg Gly Phe
                35                  40                  45

Phe Tyr Thr Lys Pro Thr
                50

<210> SEQ ID NO 54
<211> LENGTH: 51
<212> TYPE: PRT
<213> ORGANISM: Homo sapiens

<400> SEQUENCE: 54

Gly Ile Val Glu Gln Cys Ser Thr Ser Ile Cys Ser Leu Tyr Gln
 1               5                  10                  15

Leu Glu Asn Tyr Ser Asn Phe Val Asn Gln His Leu Cys Gly Ser
                20                  25                  30

His Leu Val Glu Ala Leu Tyr Leu Val Cys Gly Glu Arg Gly Phe
                35                  40                  45

Phe Tyr Thr Pro Lys Thr
                50

<210> SEQ ID NO 55
<211> LENGTH: 51
<212> TYPE: PRT
<213> ORGANISM: Bos taurus

<400> SEQUENCE: 55

Gly Ile Val Glu Gln Cys Cys Ala Ser Val Cys Ser Leu Tyr Gln
 1               5                  10                  15

Leu Glu Asn Tyr Cys Asn Phe Val Asn Gln His Leu Cys Gly Ser
                20                  25                  30

His Leu Val Glu Ala Leu Tyr Leu Val Cys Gly Glu Arg Gly Phe
                35                  40                  45

Phe Tyr Thr Pro Lys Ala
                50

<210> SEQ ID NO 56
<211> LENGTH: 51
<212> TYPE: PRT
<213> ORGANISM: porcine

<400> SEQUENCE: 56

Gly Ile Val Glu Gln Cys Cys Thr Ser Ile Cys Ser Leu Tyr Gln
 1               5                  10                  15

Leu Glu Asn Tyr Cys Asn Phe Val Asn Gln His Leu Cys Gly Ser
                20                  25                  30

```
His Leu Val Glu Ala Leu Tyr Leu Val Cys Gly Glu Arg Gly Phe
                 35                  40                  45

Phe Tyr Thr Pro Lys Ala
                50
```